US011439771B2

(12) United States Patent
Aneas (10) Patent No.: US 11,439,771 B2
(45) Date of Patent: Sep. 13, 2022

(54) NEEDLE PROTECTION DEVICE FOR A PRE-FILLED SYRINGE WITH STAKED NEEDLE, AND SYRINGE COMPRISING SUCH A DEVICE

(71) Applicant: BIOCORP PRODUCTION, Issoire (FR)

(72) Inventor: Daniel Aneas, Menetrol (FR)

(73) Assignee: BIOCORP PRODUCTION, Issoire (FR)

( * ) Notice: Subject to any disclaimer, the term of this patent is extended or adjusted under 35 U.S.C. 154(b) by 273 days.

(21) Appl. No.: 16/493,496

(22) PCT Filed: Mar. 16, 2018

(86) PCT No.: PCT/EP2018/056648
§ 371 (c)(1),
(2) Date: Sep. 12, 2019

(87) PCT Pub. No.: WO2018/167262
PCT Pub. Date: Sep. 20, 2018

(65) Prior Publication Data
US 2020/0254190 A1    Aug. 13, 2020

(30) Foreign Application Priority Data
Mar. 17, 2017   (FR) ...................................... 1752182

(51) Int. Cl.
*A61M 5/32*      (2006.01)
*A61M 5/31*      (2006.01)

(52) U.S. Cl.
CPC .......... *A61M 5/326* (2013.01); *A61M 5/3204* (2013.01); *A61M 2005/312* (2013.01)

(58) Field of Classification Search
CPC ........ A61M 5/3272; A61M 2005/3267; A61M 5/3271; A61M 5/3204; A61M 2005/312
See application file for complete search history.

(56) References Cited

U.S. PATENT DOCUMENTS

| 9,962,497 B2 | 5/2018 | Takemoto |
| 10,549,048 B2 | 2/2020 | Takemoto et al. |
| 2013/0296798 A1* | 11/2013 | Roberts ................. A61M 5/326 604/198 |

(Continued)

FOREIGN PATENT DOCUMENTS

| EP | 3106194 A1 | 12/2016 |
| FR | 3031904 A1 | 7/2016 |

(Continued)

OTHER PUBLICATIONS

Search Report for International Application No. PCT/EP2018/056648 dated Jun. 13, 2018.

(Continued)

*Primary Examiner* — Emily L Schmidt
(74) *Attorney, Agent, or Firm* — Pearne & Gordon LLP (57) ABSTRACT

The invention relates to a needle protection device for a pre-filled syringe with staked needle. This device comprises a blocking mechanism, comprising means for fastening to a syringe body, a needle shield, into which the needle can be driven, and an after-use safety system comprising a sleeve defining a central axis along which it is movable and means for resiliently loading the sleeve in a forward position in which it is able to cover the needle. The sleeve comprises an outer tube and a coaxial inner tube that are manufactured in one piece by injection molding, while the outer tube is arranged so as to cooperate with the blocking mechanism, and the inner tube is detachable from the outer tube and axially connected in translation with the needle shield.

9 Claims, 5 Drawing Sheets

(56) References Cited

U.S. PATENT DOCUMENTS

| | | |
|---|---|---|
| 2016/0001006 A1 | 1/2016 | Takemoto et al. |
| 2016/0015905 A1 | 1/2016 | Fournier et al. |
| 2016/0243315 A1* | 8/2016 | Perche ............... A61M 5/3204 |
| 2018/0021524 A1* | 1/2018 | Takemoto ........... A61M 5/3243 604/198 |
| 2018/0104421 A1 | 4/2018 | Wittland et al. |
| 2018/0126091 A1 | 5/2018 | Fraas et al. |
| 2018/0147366 A1 | 5/2018 | Aneas |
| 2018/0161512 A1 | 6/2018 | Wittland et al. |
| 2018/0161516 A1 | 6/2018 | Wittland et al. |
| 2018/0177955 A1 | 6/2018 | Aneas |

FOREIGN PATENT DOCUMENTS

| | | |
|---|---|---|
| WO | 2013134465 A1 | 9/2013 |
| WO | 2014131985 A1 | 9/2014 |
| WO | 2014141470 A1 | 9/2014 |
| WO | 2015022787 A1 | 2/2015 |
| WO | 2016120185 A2 | 8/2016 |
| WO | 20160120185 A2 | 8/2016 |
| WO | 2016158627 A1 | 10/2016 |
| WO | 2016202498 A1 | 12/2016 |
| WO | 2016202510 A1 | 12/2016 |
| WO | 2016202614 A1 | 12/2016 |
| WO | 2016206862 A1 | 12/2016 |
| WO | 2016207196 A1 | 12/2016 |

OTHER PUBLICATIONS

Search Report for French Application No. FR 1752182 dated Nov. 21, 2017.

* cited by examiner

NEEDLE PROTECTION DEVICE FOR A PRE-FILLED SYRINGE WITH STAKED NEEDLE, AND SYRINGE COMPRISING SUCH A DEVICE

CROSS-REFERENCE TO RELATED APPLICATIONS

This is the National Stage of PCT international application PCT/EP2018/056648, filed on Mar. 16, 2018, which claims the priority of French Patent Application No. 17 52182, filed Mar. 17, 2017, both of which are incorporated herein by reference in their entirety.

The invention relates to a needle protection device for a syringe of the pre-filled syringe with staked needle type. The invention also relates to a syringe comprising such a device.

A prefilled syringe with staked needle is a single-use syringe, comprising a metal hypodermic needle, which is glued to the inside of a channel defined in the syringe body. The syringe is prefilled, in that the nurse does not need to fill the syringe, for example from a vial, before performing the injection.

In a manner known in itself in the medical field, syringes with staked needles are equipped with a needle shield, inside which the needle is buried. Often, the needle shield is made from rubber or elastomer. So-called "rigid" needle shields exist, comprising an inner body made from a flexible material and an outer body made from a rigid material. The inner body provides the sealing of the active ingredient contained inside the syringe relative to the outside and the outer body protects the needle from impacts. In particular, the outer body can prevent the needle from twisting.

Syringes with staked needles must preferably incorporate a post-use safety system. This post-use safety system is intended to prevent any contact with the needle once the injection is complete. It therefore seeks to limit the risk of contamination by the needle and therefore the transmission of diseases, such as HIV. For information, such a system is legally required in countries such as the United States and Canada.

To that end, the applicant company, BIOCORP CORPORATION, has developed a protective device that is specific in that it comprises, on the one hand, a rigid needle shield made up of a flexible part enveloped in a rigid sheath, and on the other hand, a post-use safety device made up of a sleeve and a spring. This protective device is in particular described in international applications WO 2016/120185 A1 and WO 2016/207196 A1.

This device is open to improvement in several respects.

The first point relates to the manufacturing of the sleeve. The latter has cylindricality flaws due to the fact that the plastic injection method used an off-centered injection point relative to the central axis of the sleeve. Indeed, due to the hollow and tubular geometry of the sleeve, it was not possible to inject the material through the center.

The second point relates to the placement of the needle shield on the end of the syringe body. Indeed, during the assembly of the device, the flexible part of the needle shield was compressed lengthwise so as to provide the sealing with the syringe body. The compression was done by pressing at the end of the flexible part of a lug formed inside the rigid sheath of the needle shield. This bearing surface was not necessarily suitable, in that this could cause assembly flaws. In particular, the flexible part of the needle shield could twist during assembly.

The third point relates to the fact that with this device, nothing prevented manual withdrawal of the sleeve. The sleeve could therefore be moved into the end-of-injection configuration, in which configuration it was locked. In such a scenario, the needle cannot be exposed and the syringe is unusable, which is clearly not desirable. Such a movement could take place during the placement inside housings defined in the standard substrates usable for transport and packaging (better known as "nest"), during the conveyance, wrapping, transport phases, or even before use.

The fourth point relates to the fact that users had trouble understanding which part was detachable and how to detach it.

The fifth point relates to the "coring" phenomenon. This phenomenon occurs during a relative movement between the needle and the needle shield: the beveled shape of the tip of the needle tends to "hollow out" the component material of the needle shield and generates elastomer shavings that may fall inside the needle.

Lastly, the sixth point relates to the syringe sterilization step. In a manner known in itself, the syringes, equipped with protection devices, are sterilized with a specific gas, in particular ETO (ethylene oxide). Next, some prefilled syringes are sterilized, with their contents, in an autoclave, for example with steam. During this step, the pressure increase inside the inner chamber of the flexible part of the needle shield could cause loosening of the needle shield, and this loosening could lead to a sealing defect with the syringe body. This phenomenon is called "pop-off". Additionally, the same effect could be obtained during an impact, vibrations (for example during transport) leading to the sliding of the needle shield.

Thus, the invention intends to propose an improved needle protection device.

To that end, the invention relates to a needle protection device for a pre-filled syringe with staked needle, the device comprising a blocking mechanism, comprising means for fastening to a syringe body, a needle shield, into which the needle can be driven, an after-use safety system, comprising a sleeve defining a central axis along which it is movable and means for elastically loading the sleeve in a forward direction in which it is able to cover the needle. According to the invention, the sleeve comprises an outer tube and a coaxial inner tube that are manufactured in one piece by injection molding, while the outer tube is arranged so as to cooperate with the blocking mechanism, and the inner tube is detachable from the outer tube and axially connected in translation with the needle shield.

WO 2016/158 627 A1, which may be considered the closest state of the art, discloses a needle protection device, in which the outer body of the (rigid) needle shield is removably fastened with the sleeve. In particular, the outer body delimits a radial shoulder for receiving an inner peripheral rim formed at one axial end of the sleeve. In paragraph [0051] of WO 2016/158 627 A1, it is stated that the inner tube 40 is made from a material whose rigidity is greater than that of the needle shield 46, for example a resin. As a result, the inner tube 48 is mounted outside the needle shield 46 such that the body of the needle protector 34 is configured so as to have a sufficient rigidity. Thus, the user can easily push the needle shield 46 into the outer tube 32 by means of the inner tube 48 or detach the needle shield 46 plus inner tube 48 assembly from the needle 16. The content of this paragraph [0051], as well as the depiction of FIG. 3, for example, clearly indicate that the inner tube 48 and the outer tube 32 are not manufactured in a single piece by injection molding.

WO 2014/131985 A1 discloses a needle protection device comprising a rigid needle shield, in which the outer body is removably attached to the blocking mechanism by means of frangible bridges and in which the outer body and the inner body of the needle shield are axially connected in translation. The axial end edge of the outer body is folded down toward the inside to fixedly maintain the inner body.

WO 2013/134465 A1 discloses a needle protection device comprising an after-use safety system and a flexible needle shield, inside which the needle is driven. The after-use safety system comprises an outer sleeve and a spring. A blocking mechanism is immobilized on the syringe body. This blocking mechanism comprises two radial pins each inserted into a radial guide opening of the sleeve.

US 2015/0246182 A1 discloses a needle protection device, in which a cap is removably attached to the sleeve and is axially connected to the (flexible) needle shield. In particular, the cap comprises two pushbuttons used to pinch the needle shield to remove it. The number of parts used and their complexity make this device expensive to manufacture, and therefore not very interesting from an industrial perspective. Furthermore, if the user rotates the cap (even slightly) during the removal of the needle shield, there is a risk of coring.

WO 2015/022 787 A1 discloses a needle protection device, in which the (flexible) needle shield is detachably connected to the sleeve. In particular, the needle shield delimits a peripheral groove inside which an inner peripheral rib of the sleeve is received, which is formed at an axial end of the latter.

WO 2016/206 862 A1 discloses an example after-use safety system for a syringe with staked needle. This system comprises, in a manner known in itself, an outer protective sleeve and a spring arranged to elastically charge the sleeve in the forward direction, i.e., distally relative to the syringe body. The sleeve delimits a radial guide opening for a pin formed on a blocking mechanism mounted fixedly at one end of the syringe body.

WO 2016/202 614 A1 discloses a needle protection device in which the needle shield is provided in the form of a cap made from a flexible material. This cap comprises an outer part configured to radially cover the sleeve and an inner coaxial part inside which the needle is driven. The cap is removably attached to the sleeve owing to a clipping system. WO 2016/202 510 A1 has substantially the same technical teaching.

WO 2016/202 498 A1 differs from the two previous documents, in that the needle protector has two parts. It comprises a flexible inner part inside which the needle can be driven and an outer part arranged coaxially around the sleeve. The outer part is connected axially in translation with the inner part and is clipped with the sleeve.

None of the prior art documents discloses a protective sleeve comprising an inner tube and an outer tube manufactured in one part by injection molding. The needle protection device according to the invention is therefore simpler and less expensive to manufacture than the devices of the prior art. Furthermore, the inner tube of the sleeve opposes the backward movement of the outer tube, i.e., toward the syringe body. Thus, the sleeve is immobilized in translation as long as the removable part of the latter, i.e., the inner tube, is still in place. Thus, there is no risk that the outer tube of the sleeve will be in the end-of-injection configuration in error, i.e., following an incorrect manipulation or an impact.

According to advantageous, but optional aspects of the invention, such a device may incorporate one or more of the following features, considered in any technically allowable combination:

The needle shield comprises a collar inserted axially between the blocking mechanism and the inner tube of the sleeve.

In this way, the collar forms an axial stop for the inner tube of the sleeve and opposes the withdrawal of the sleeve as long as the inner tube has not been detached. Additionally, the inner tube of the sleeve opposes, to within any axial play, the sliding of the needle shield in the forward direction around the syringe body, for example under the effect of vibrations caused during transport. Furthermore, there is no risk of pop-off during the sterilization operation in the autoclave, when the latter is done, since the inner tube of the sleeve opposes the loosening of the needle shield, i.e., the movement of the needle shield in a distal direction relative to the syringe body. Also, when one presses on the inner tube during assembly, the force is primarily transmitted by the inner tube of the sleeve, then by the collar. The share of the needle shield in the transmission of forces is therefore in the minority, such that the risk of the needle shield twisting or going askew is reduced, or even eliminated.

The outer tube and the inner tube are attached to one another by frangible bridges.

The bridges are configured to be broken when a torque is applied, on the inner tube of the sleeve, around the central axis thereof and the outer tube is manually retained, i.e., immobilized in rotation. In other words, the bridges are broken by imposing a relative rotation between the inner tube and the outer tube. The inner tube rotates freely (around its axis) relative to the needle shield. The inner tube can therefore be pivoted around its axis without rotating the needle shield. The sleeve, and more particularly the inner tube, has a mechanical protection function with respect to the needle. It prevents the latter from twisting.

The frangible bridges are formed at an axial end of the outer tube.

Contrary to the device of WO 2016/120185 A1 and WO 2016/207196 A1, the bridges are arranged outside the outer tube, such that the force to be applied to break the bridges is lower.

The inner tube comprises a closed end.

Given that the outer tube and the inner tube are a same piece, having this closed end has the advantage that the material injection point during the injection molding method can be provided on the central axis of the sleeve, which make it possible to obtain a homogeneous distribution of material, with no cylindricality flaw and to avoid any weld line. Furthermore, this makes it possible to completely cover the needle shield. Thus, the needle shield is completely isolated from the outside, and in particular from dust. This is more aesthetically pleasing for users, i.e., the medical staff.

The inner tube has a minimum outer diameter strictly smaller than an outer diameter of a distal end part of the blocking mechanism.

Owing to this feature, the mounting of the needle shield around the end of the syringe body is made easier. Indeed, we indicated above that the collar of the needle shield was inserted axially between the inner tube and the blocking mechanism. The needle shield includes a skirt intended to marry the shape of the end of the syringe body. During the mounting of the needle shield, the collar is therefore compressed between the blocking mechanism and the inner tube. Due to the aforementioned difference in diameter, the forces respectively applied by the blocking mechanism and the inner tube are off-centered relative to one another, which in fact creates a torque oriented outward, i.e., said torque tends to open the skirt of the needle protector. In other words, the resultant forces exerted by the inner tube on the collar are further from the central axis than the resultant forces exerted by the blocking mechanism on the collar. The resultant torque favors the fitting of the skirt of the needle shield around the end of the syringe body and prevents the needle shield from collapsing against the end of the syringe body.

The inner tube is opaque and the outer tube is transparent.

This feature makes it possible to meet a user need according to which the detachable part of the device must be clearly identifiable and according to which the needle must remain visible once the needle shield has been removed.

The inner tube and the outer tube have a different surface state.

This differentiated surface state makes it possible to create the illusion of two separate parts, even if the inner tube and the outer tube are in fact a same part manufactured by injection molding. Advantageously, the plastic used during the injection has a substantially transparent base, or at least translucent. The surfaces of the mold used to manufacture the sleeve are made so as to obtain a different surface state (roughness) between the inner tube and the outer tube. In particular, the outer tube has very smooth surfaces, owing to a method commonly called mirror polish, which gives it a very transparent appearance. Conversely, the inner tube has rougher surfaces, i.e., a more coarse, or more raw, surface state, which is commonly called wood grain, and which imparts an opaque appearance.

The inner tube comprises gripping fins.

These gripping fins form an additional index for the user as to which part of the device is detachable. Additionally, the fins make it possible to define a gripping segment with a larger diameter (relative to the rest of the tube), which means that the force to be provided to break the frangible bridges is necessarily lower, due to the increase in the lever arm.

The blocking mechanism comprises at least one pin engaged in a radial guide opening of the first tube.

The invention also relates to a prefilled syringe with staked needle, comprising a device as previously described.

Preferably, the blocking mechanism is mounted freely rotating around a syringe body.

Advantageously, the blocking mechanism is mounted with radial play around the needle shield.

Thus, the blocking mechanism can rotate freely in the configuration with the device mounted on the syringe body. The blocking mechanism plus sleeve assembly therefore rotates completely freely around the syringe body and around the needle shield. By making the blocking mechanism completely freely rotating around the needle shield, the risk of coring is completely eliminated during all usage phases of the syringe.

During an injection, the sleeve is immobilized in rotation in contact with the skin. Conversely, the blocking mechanism can orient itself relative to the sleeve to provide the guiding of the pins in the corresponding radial openings of the sleeve. Additionally, since there is no relative rotation of the sleeve with respect to the blocking mechanism, it is impossible, at the end of injection, to rearm the sleeve in the position covering the needle.

The invention and other advantages thereof will appear more clearly in light of the following description of one embodiment of a needle protection device, provided solely as an example and done in reference to the appended drawings, in which.

Figure 1:
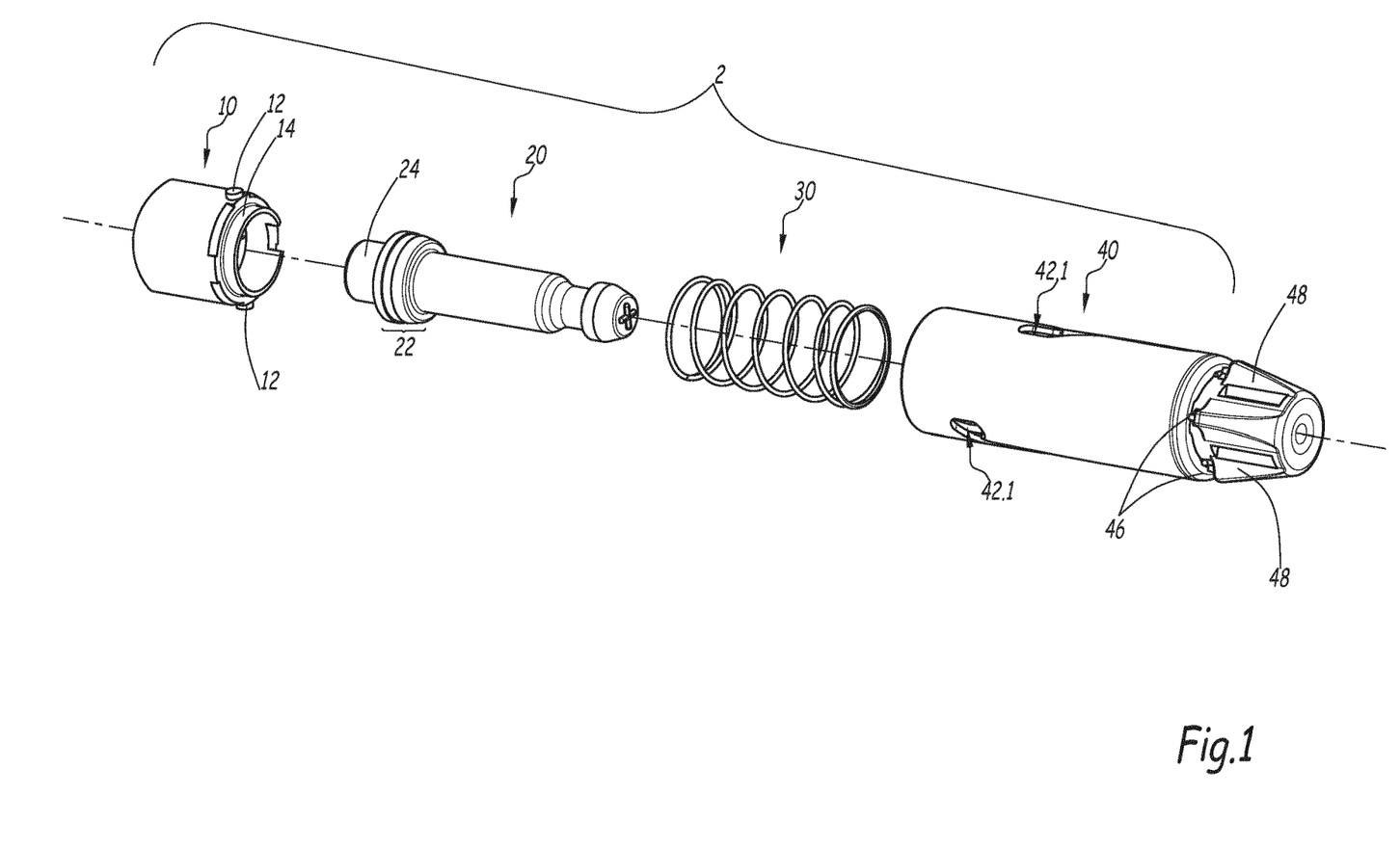
FIG. 1 is an exploded perspective view of a needle protection device according to the invention, intended to be mounted on a prefilled syringe with staked needle.
Figure 2:
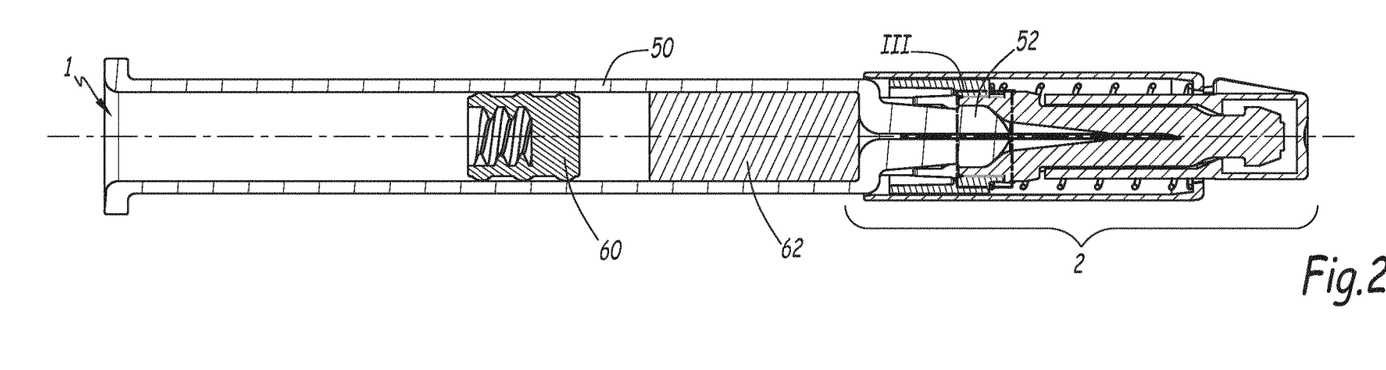
FIG. 2 is a sectional view of the device of FIG. 1 in the configuration assembled on a syringe body.

FIGS. 1 to 4 show a needle protection device 2. As shown in FIG. 2, the device 2 is configured to be mounted on a syringe 1 body 50, in particular at one end 52 of the syringe body 50, which is commonly called the tip of the syringe. The syringe 1 is a prefilled syringe with staked needle. It comprises a piston 60 (or piston seal) screwed to a piston rod (not shown). An active ingredient 62 is contained inside the syringe body 50. The end part 52 of the syringe body 50 delimits a channel 54 inside which a hypodermic needle 58 is staked. The needle 58 is made from metal and has a beveled end.

Advantageously, the syringe body 50 is standard, i.e., it is the majority syringe body sold, at least in Europe, for this type of application. For information, this type of syringe body represents the majority of the market shares in Europe.

The needle protection device 2 defines a central axis X2. It comprises a blocking mechanism 10, a needle shield 20, a spring 30 and a sleeve 40.

In the present document, a proximal (or rear) direction is defined as a direction parallel to the central axis X2 oriented toward the syringe body 50. Conversely, a distal (or forward) direction designates a direction parallel to the axis X2 but oriented away from the syringe body 50.

Additionally, the adjective "radial" refers to a surface perpendicular to the axis X2, while the adjective "axial" refers to a surface parallel to the axis X2.

The blocking mechanism 10, which may also be known as a collar, has a geometry substantially of revolution. It comprises means 16 for attachment on the syringe body 50. These attachment means 16 comprises resilient tabs, of which there are three in the example and which are configured to snap, i.e., to "clip", around the end part 52 of the syringe body 50. To that end, the end part 52 delimits a neck 56 against which the resilient tabs 16 can be attached. Advantageously, the blocking mechanism 10 comprises at least one, preferably two radial pins 12 that protrude radially outward. In the example, the pins 12 are diametrically opposite.

The blocking mechanism 10 comprises a shoulder defining a distal end part 14, the outer diameter D14 of which is reduced relative to the rest of the blocking mechanism.

The blocking mechanism 10 of the needle protection device 2 is easier to manufacture than the collar of the device of WO 2016/120185 A1. Indeed, in this publication, the collar was manufactured in a single piece with a rigid sheath surrounding the needle sheath. Yet when the core used for molding was removed, the inner reliefs of the collar formed an undercut that opposed this removal, which caused pulling out of material. Conversely, the blocking mechanism 10 is manufacturing according to an injection molding method using two separate cores, which are each removed on one side of the blocking mechanism, so as to avoid any pulling out of material. This is made possible since the tube 44 and the blocking mechanism 10 are not attached to one another, at least not directly like in WO 2016/120185 A1.

The pins 12 of the blocking mechanism 10 are advantageously engaged in corresponding radial openings 42.1 of the sleeve 40. The openings 42.1 are substantially Y-shaped. They are identical to those described in publications WO 2016/120185 A1 and WO 2016/207196 A1, which are integrated by reference, which is why they are not described in more detail. The sleeve 40 is connected in rotation with the blocking mechanism 10 around the central axis X2 due to the cooperation between the pins 12 and the openings 42.1. Furthermore, the cooperation between the pins 12 and the openings 42.1 of the sleeve prevents moving the sleeve 40 in the distal direction relative to the blocking mechanism 10, in particular since, in the storage configuration, the pins 12 abut in the openings 42.1.

Advantageously, the openings 42.1 serve as a passage for sterilization gases, such as ethylene oxide, during the sterilization of the syringe.

The sleeve 40 comprises an outer tube 42 delimiting the openings 42.1 and an inner tube 44. The outer tube 42 and the inner tube 44 are manufactured in one piece by injection molding. The inner tube 44 is arranged coaxially inside the outer tube 42 and protrudes axially, on the distal side, relative to the outer tube 42.

Cleverly, the inner tube 44 of the sleeve 40 opposes the loosening of the needle shield 20, i.e., the movement of the needle shield 20 in a distal direction relative to the syringe body 50, during the sterilization operation in the autoclave. Additionally, the inner tube 44 opposes the sliding of the needle shield 20 around the end 52 of the syringe body 50, due to the vibrations caused during the transport or the like.

The sleeve 40, and more particularly the inner tube 44, also serves to protect the needle 58, and in particular to prevent the needle from twisting. It can be likened to a rigid needle shield.

The outer tube 42 and the inner tube 44 are attached to one another by frangible bridges 46. In the example, there are four frangible bridges 46, or spurs.

Advantageously, the bridges 46 are configured to be broken when a torque is applied, on the inner tube 44 of the sleeve 40, around the central axis thereof and the outer tube 42 is manually retained, i.e., immobilized in rotation. The inner tube 44 rotates freely (around its axis) relative to the needle shield 20. The inner tube can therefore be pivoted around its axis without rotating the needle shield 20. Indeed, it is imperative not to create a rotational movement of the needle shield 20 around the needle 58 because the beveled shape of the tip of the needle tends to "hollow out" the component material of the needle shield and generate elastomer shavings that may fall inside the needle ("coring" phenomenon).

In particular, the frangible bridges 46 are formed at a distal end 42.2 of the outer tube 42. They are therefore arranged outside the inner space of the tube 42. Relative to the device of WO 2016/120185 A1 and WO 2016/207196 A1, the force to be applied to break the bridges 46 is therefore lower.

Advantageously, the distal end 42.2 comprises a beveled inner edge 42.20, flared toward the inside of the tube 42.

Preferably, the inner tube 44 is not a through tube, since it advantageously comprises an end wall 44.2 closing off the distal end of the tube 44. Owing to this wall 44.2, the material injection point 44.3 during the injection molding can be positioned at the central axis, or axis of revolution, of the sleeve 40. This guarantees a homogeneous distribution of material in the mold and very low cylindricality allowances. Furthermore, given that a single centralized injection point is used, there is no weld line. Traditionally, the weld lines are the lines at which the material injected into the mold comes together. Not having weld lines is particularly advantageous, since the weld lines (or junction lines) traditionally form mechanical weak spots. Additionally, this wall 44.2 makes it possible to completely cover the needle shield 20 and therefore protects from dust, which is more esthetically pleasing, but important in a hospital setting.

Reference D44 denotes the minimum outer diameter of the inner tube 44. This diameter may in particular be measured at the proximal end of the tube 44.

Advantageously, the inner tube 44 includes an axial retaining means, formed in the example by at least one, preferably several inner ribs 44.1 that extend, by sector, along a peripheral (orthoradial) direction around the central axis of the device.

Fins 48 are formed on the visible part of the inner tube 44, i.e., the part of the inner tube 44 arranged outside the outer tube 42. These fins 48 are gripping fins inviting the user to manipulate the inner tube 44 to detach it from the outer tube 42. An enclosure surface of the fins 48 (not shown) has a diameter smaller than or equal to the outer diameter of the outer tube 42 of the sleeve 40. In this way, the fins 48 do not hinder the placement (and removal) of the syringes inside the "nests".

The needle shield 20 is arranged with radial play inside the inner tube 44 of the sleeve 40, such that the tube 44 can rotate freely around the needle shield 20. The needle shield 20 is made from a flexible material, such as an elastomer, in particular a thermoplastic elastomer (TPE), or a rubber. In particular, the component material of the needle shield 20 is such that the needle 58 of the syringe can be driven inside the latter. Additionally, this material is permeable to gases, such that the ethylene oxide (ETO) can penetrate the inside of the skirt 24 during sterilization.

The needle shield 20 comprises, on the proximal side, a skirt 24 intended to be fitted around the tip 52 of the syringe and thus to marry the shape of the tip 52.

The needle shield 20 further includes, on the distal side, a part with a reduced section and a peripheral shoulder 26, widening the outer diameter of the needle shield 20 toward the distal side. The shoulder 26 is configured to cooperate with the retaining means 44.1 of the tube 44. In particular, the rib 44.1 is provided to abut against the shoulder 26 when the tube 44 is axially detached from the tube 42. Thus, the needle shield 20 and the inner tube 44 of the sleeve 40 are axially connected in translation. The connecting means between the needle shield 20 and the inner tube 44 are clearly not limited to the described example embodiment, and other solutions can be implemented to provide an axial connection between the needle shield 20 and the inner tube 44 of the sleeve 40.

The needle shield 20 further includes a collar 22 intended to be interposed axially between the inner tube 44 and the blocking mechanism 10, in particular between the proximal end of the inner tube 44 and the distal end part 14 of the blocking mechanism 10.

The collar 22 comprises, on the distal side, a slope 22.1, or bevel, and on the proximal side, a radial edge 22.2. The collar 22 advantageously forms an axial stop for the inner tube 44 of the sleeve 40 and opposes the withdrawal of the sleeve 40 as long as the inner tube 44 has not been detached. In practice, for technical reasons, axial play J nevertheless exists between the end of the tube 44 and the collar 22. This play J is cleverly chosen to be smaller than the injection length of the needle 58, i.e., the length over which the needle 58 is driven into the needle shield 20. As a result, there is no risk of the needle 58 leaving the needle shield during the sterilization operation in the autoclave. In the example, the play J is approximately 0.4 mm.

The spring 30 is a spiral spring extending between a shoulder of the blocking mechanism 10 and the distal end 42.2 of the outer tube 42, which extends radially toward the inside of the tube. The spring 30 forms a means for resiliently loading the outer tube 42 into a forward position in which it is able to cover the needle 58.

Advantageously, the outer tube 42 is transparent, while the inner tube 44 is opaque. This gives the illusion that the outer tube 42 and the inner tube 44 are two different parts. This advantageously satisfies a user need according to which the detachable part of the device 2, i.e., the tube 44, must be clearly identifiable and according to which the needle 58 must remain visible once the needle shield 20 has been removed.

In the example, the illusion comes from a distinct surface treatment, in the mold, between the inner tube 44 and the outer tube 42. The plastic used at the base of the mold is substantially transparent, or at least translucent. The surfaces of the mold used to manufacture the sleeve 40 are made so as to obtain a different surface state (roughness) between the inner tube 44 and the outer tube 42. In particular, the outer tube 42 has very smooth surfaces, owing to a method commonly called mirror polish, which gives it a very transparent appearance. Conversely, the inner tube 44 has rougher surfaces, i.e., a more coarse, or more raw, surface state, which is commonly called wood grain, and which imparts an opaque appearance.

In the example, and as mentioned in WO 2016/120185 A1, the device 2 has a maximum (outer) diameter that is less than or equal to 9.3 mm. This makes it possible for the syringe bodies 50, with their device 2, to enter the housings of a standard support (or "nest"), i.e., making up the majority of the market and the housings (holes) of which have a diameter of 9.3 mm.

The assembly of the device 2 is done as follows. The needle shield 20 is mounted inside the sleeve 40. To that end, the needle shield 20 is inserted through the proximal end of the sleeve 40 inside the inner tube 44. The needle shield 20 then compresses to pass the rib 44.1 of the inner tube 44 and becomes positioned naturally in the position of FIG. 4.

Next is the assembly of the spring 30 and that of the blocking mechanism. In particular, the blocking mechanism 10 is inserted inside the sleeve 40, in the example by force. Alternatively, axial slots may guide the pins 12 of the blocking mechanism 10 to the guide openings 42.1. The order in which the assembly steps above are carried out is not important.

The assembly of the device 2 on the syringe body 50 is done as follows. The assembly method is identical, or otherwise equivalent to the current method.

Figure 5:
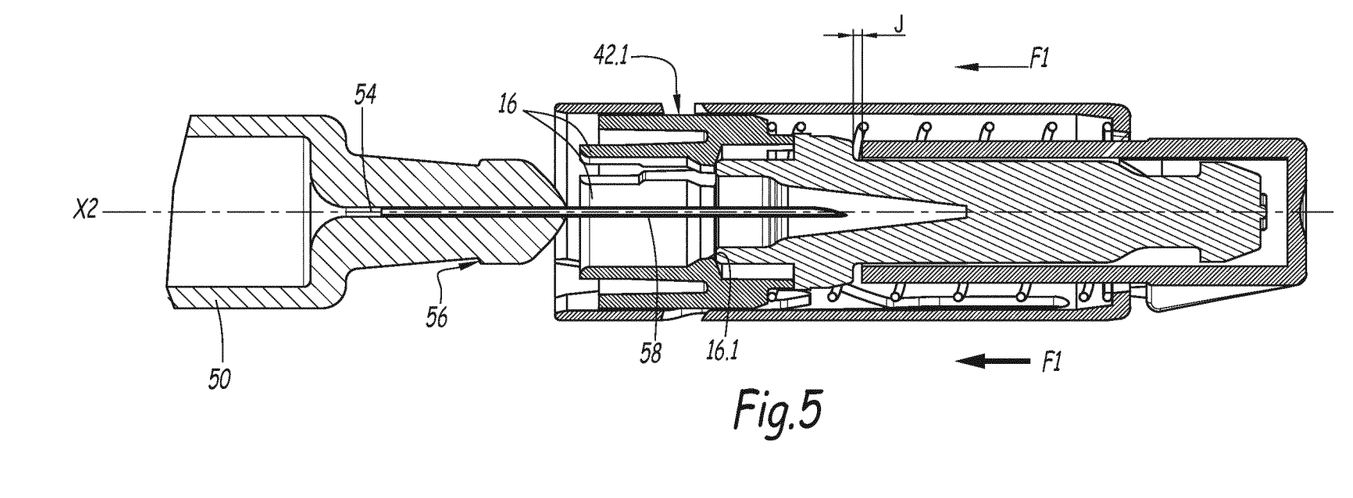
FIGS. 5 to 8 are sectional views successively showing assembly steps of the device of FIGS. 1 to 3 on a body of a syringe with staked needle.

The device 2 is brought axially closer to the end 52 of the syringe body 50 so as to drive the needle 58 inside the needle shield 20. This approach movement is illustrated by arrows F1 in FIG. 5. The resilient tabs 16 snap around the end part 52, in particular owing to the cooperation between the shoulder 56 and the protrusions 16.1 of the tabs 16. In parallel, the collar 22 of the needle shield 20 is compressed axially between the inner tube 44 of the sleeve 40 and the distal end part 14 of the blocking mechanism 10.

Given that, when one presses on the inner tube 44 during the assembly, the force is transmitted to the collar 22, the risk of the needle shield 20 twisting or going askew during the assembly is reduced, or even eliminated.

Figure 6:
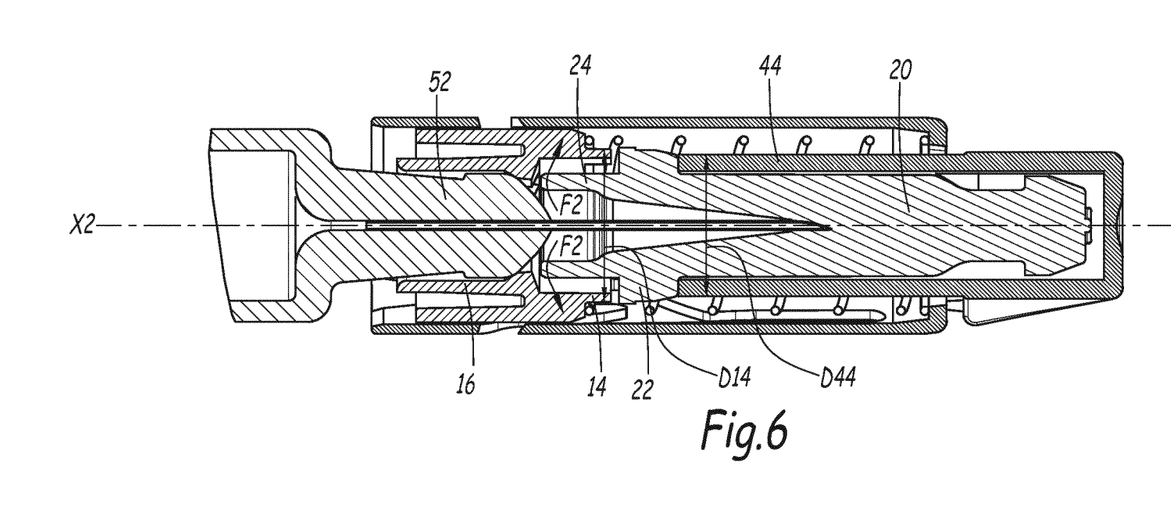

Furthermore, the diameter D14 of the distal end part 14 of the blocking mechanism 10 being greater than the diameter D44 of the inner tube 44, a torque is generated. This torque tends to move the opening of the skirt 24 away from the needle shield 20, as shown by the arrows F2 in FIG. 6. The skirt 24 then fits more easily around the end part 52 of the syringe body 50.

Figure 3:
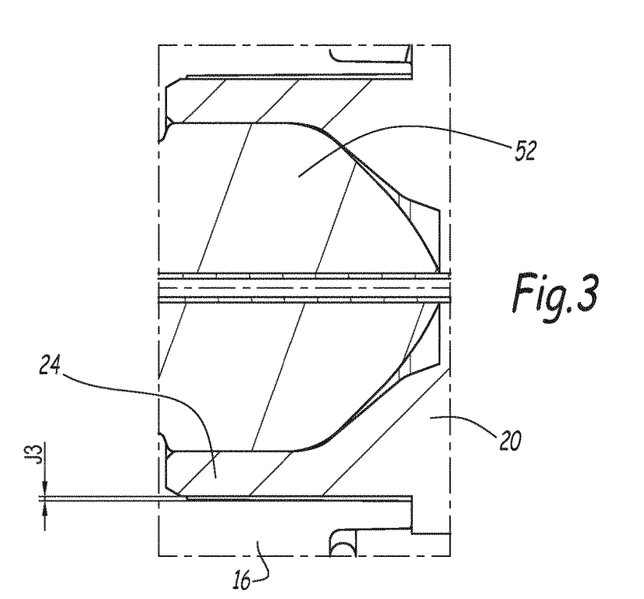
FIG. 3 is a detail of box III of FIG. 2.
Figure 4:
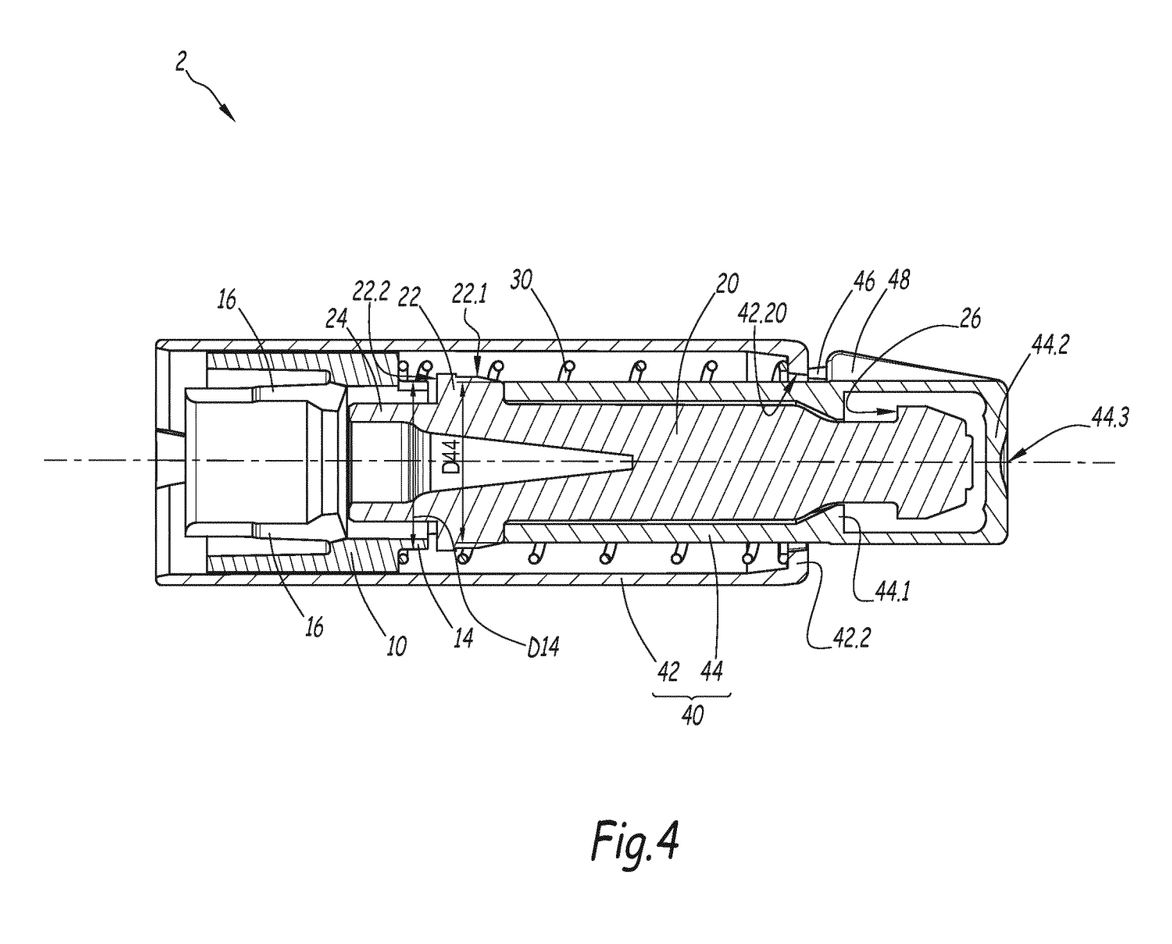
FIG. 4 is a sectional view of the device of FIGS. 1 and 2 shown alone.

As shown in FIG. 3, radial play J3 exists between the needle shield 20 and the blocking mechanism 10. The blocking mechanism 10 is therefore free to rotate around the needle shield 20, and in particular around the skirt 24. The sleeve plus blocking mechanism assembly therefore rotates completely freely around the syringe body 50.

Figure 7:
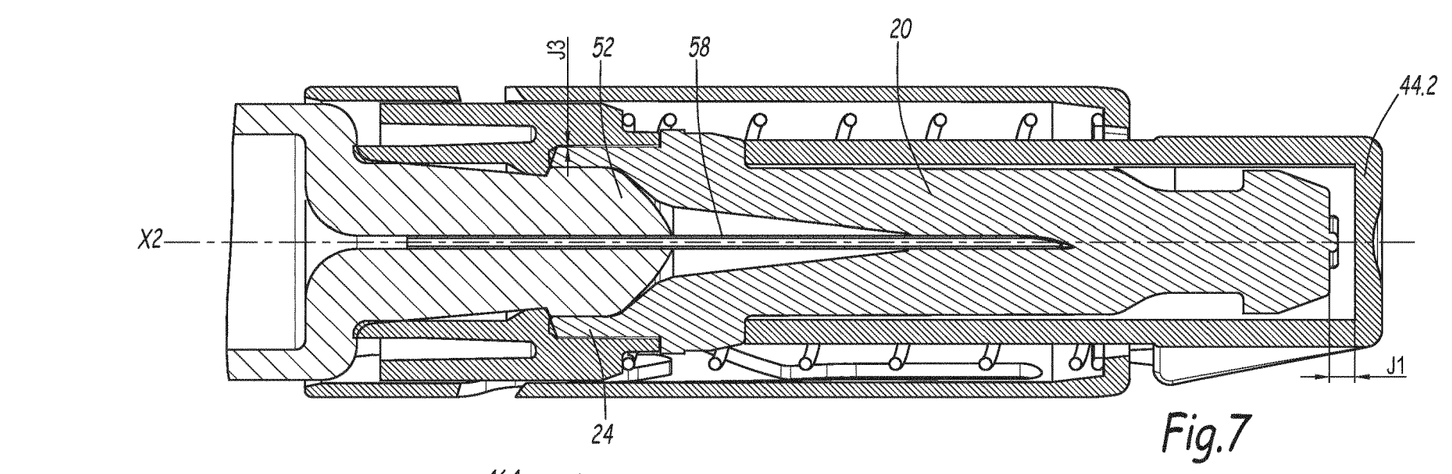
Figure 8:
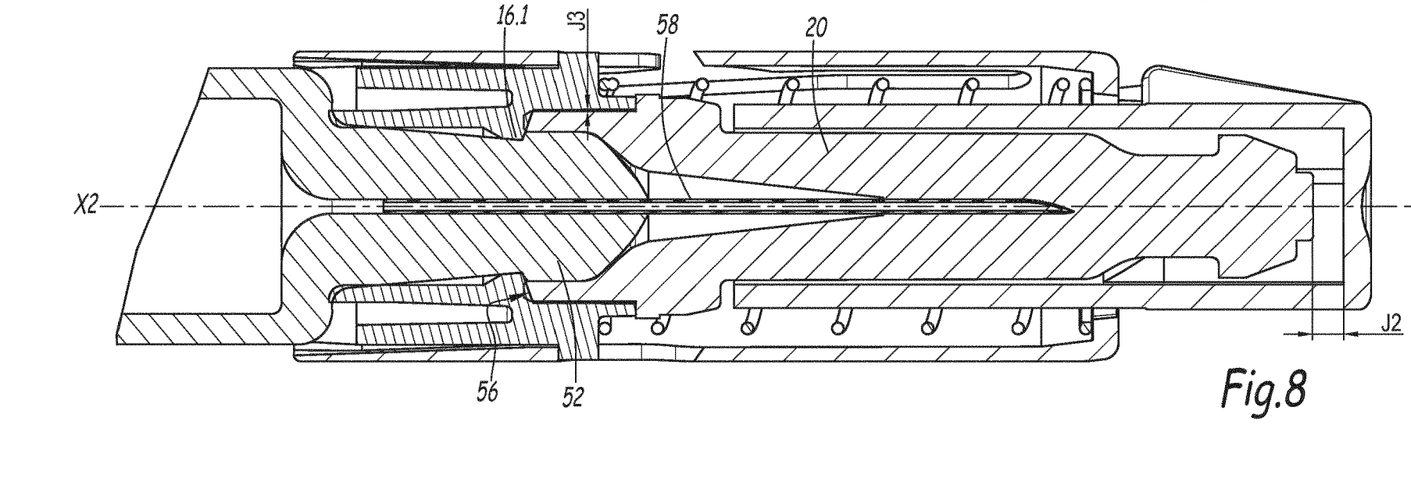

Once the pressure is released on the device 2, the spring 30 relaxes slightly, which causes the sleeve 40 to move forward by several millimeters. This is particularly visible in looking at the difference in axial play between the distal end of the needle shield 20 and the end wall 44.2 of the inner tube 42. Indeed, the axial play J2 in FIG. 8 is greater than the axial play J1 in FIG. 7. This slight movement makes it possible to separate the functional surfaces of the rib 44.1 from the outer surface of the needle shield 20, which limits the risk of catching of the needle shield with the tube 44 when the tube 44 is rotated to be detached, and therefore the risk of coring.

Before performing an injection, the user rotates the inner tube 44 around its axis, so as to break the bridges 46. Next, the user can detach the inner tube 44 through an axial withdrawal movement and at the same time removes the needle shield 20. It will therefore be understood that the needle shield 20 is removed in two stages. This was partially the subject matter of application WO 2016/120185 A1. The forces related to the removal of the needle shield are thus broken down. Conversely, in the prior art, the bridges were broken by pulling on the detachable part, such that the axial forces necessary to break the bridges were added to those necessary to move the needle shield, and the tensile force was therefore relatively high.

Advantageously, the beveled edge 42.20 formed at the distal end 42.2 of the outer tube 42 opposes the reinsertion of the needle shield 20 inside the tube 42 and in particular abuts against the blunt edge 22.2 of the collar. The user is thus discouraged from placing the assembly comprising the tube 44 and the needle shield 20 back inside the tube 42 after the injection, which eliminates the risk of being stung after injection.

Conversely, due to its incline flared toward the inside of the tube 42, the edge 42.20 does not oppose the movement of the needle shield 20 outside the tube 42, by sliding of the incline 22.1 against the edge 42.2.

The steps to perform the injection of the active ingredient into a patient's body, i.e., the usage method of the syringe, are identical to those disclosed in WO 2016/120185 A1 and WO 2016/207196 A1. This is why, for concision reasons, these steps are not described again in this document.

In an alternative that is not shown, the device includes an inscription (marking), for example an icon or an arrow, to indicate to the user what maneuver to perform to remove the needle shield 20. For example, this marking can be an arrow, in two directions or one direction, indicating a rotational movement. Another arrow can be provided to indicate the pulling movement.

According to another alternative that is not shown, the visible part of the inner tube 44, i.e., the part of the tube 44 arranged outside the tube 42, comprises at least one, preferably several radial openings, favoring the passage of the sterilization gas with ethylene oxide (ETO).

The features of the embodiment and alternatives may be combined with one another to create new embodiments of the invention.

What is claimed is:

1. A needle protection device for a pre-filled syringe with staked needle, the device comprising:
   a blocking mechanism, comprising means for fastening to a syringe body,
   a needle shield, into which the needle can be driven,
   an after-use safety system, comprising a sleeve defining a central axis along which it is movable and means for elastically loading the sleeve in a forward direction in which it is able to cover the needle,
   wherein the sleeve comprises an outer tube and a coaxial inner tube that are manufactured in one piece by injection molding, and wherein the outer tube is arranged so as to cooperate with the blocking mechanism, while the inner tube is detachable from the outer tube and axially connected in translation with the needle shield,
   wherein the needle shield is arranged with a radial play inside the inner tube of the sleeve, such that the inner tube can rotate freely around the needle shield,
   wherein the needle shield comprises a collar, interposed axially between a distal end part of the blocking mechanism and a proximal end of the inner tube of the sleeve, and
   wherein an axial play is arranged between the proximal end of the inner tube and the collar.

2. The device according to claim 1, wherein the outer tube and the inner tube are attached to one another by frangible bridges.

3. The device according to claim 2, wherein the frangible bridges are formed at a distal end of the outer tube.

4. The device according to claim 1, wherein the inner tube comprises a closed end.

5. The device according to claim 1, wherein the inner tube has a minimum outer diameter strictly smaller than an outer diameter of the distal end part of the blocking mechanism.

6. The device according to claim 1, wherein the inner tube is opaque and the outer tube is transparent.

7. The device according to claim 1, wherein the inner tube and the outer tube have different surface states.

8. The device according to claim 1, wherein the inner tube comprises gripping fins.

9. A prefilled syringe with staked needle, comprising a needle protection device according to claim 1 and a syringe body, wherein the needle protection device is mounted on the syringe body.

* * * * *